(12) United States Patent
Metzger et al.

(10) Patent No.: US 8,444,699 B2
(45) Date of Patent: May 21, 2013

(54) METHOD AND APPARATUS FOR AUGMENTING BONE DEFECTS

(75) Inventors: Robert Metzger, Wakarusa, IN (US);
Brian M. May, Warsaw, IN (US);
Daniel E. Williamson, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 229 days.

(21) Appl. No.: 12/708,309

(22) Filed: Feb. 18, 2010

(65) Prior Publication Data

US 2011/0202141 A1    Aug. 18, 2011

(51) Int. Cl.
*A61F 2/30* (2006.01)

(52) U.S. Cl.
USPC .................................................. 623/23.46

(58) Field of Classification Search
USPC ............ 623/23.44–23.46, 23.48, 23.5–23.63, 623/23.15, 23.23, 23.18–23.26, 17.16, 16.11, 623/18.11, 19.11–19.14; 606/60, 246–248
See application file for complete search history.

(56) References Cited

U.S. PATENT DOCUMENTS

| | | | | |
|---|---|---|---|---|
| 3,605,123 A * | 9/1971 | Hahn | ......................... | 623/23.55 |
| 3,929,971 A | 12/1975 | Roy | | |
| 4,202,055 A | 5/1980 | Reiner et al. | | |
| 4,655,777 A | 4/1987 | Dunn et al. | | |
| 4,722,870 A | 2/1988 | White | | |
| 4,737,411 A | 4/1988 | Graves, Jr. et al. | | |
| 4,769,011 A | 9/1988 | Swaniger | | |
| 4,822,366 A * | 4/1989 | Bolesky | ...................... | 623/20.15 |
| 4,846,839 A * | 7/1989 | Noiles | .......................... | 623/23.46 |
| 4,861,733 A | 8/1989 | White | | |
| 4,944,757 A * | 7/1990 | Martinez et al. | ............ | 623/20.15 |
| 4,969,896 A | 11/1990 | Shors | | |
| 4,976,736 A | 12/1990 | White et al. | | |
| 5,002,578 A * | 3/1991 | Luman | ....................... | 623/22.42 |
| 5,084,051 A | 1/1992 | Tormala et al. | | |
| 5,137,535 A | 8/1992 | Keller | | |
| 5,181,928 A * | 1/1993 | Bolesky et al. | ............. | 623/22.42 |
| 5,186,162 A | 2/1993 | Talish et al. | | |
| 5,211,160 A | 5/1993 | Talish et al. | | |
| 5,290,313 A * | 3/1994 | Heldreth | ..................... | 623/20.15 |
| 5,348,788 A | 9/1994 | White | | |
| 5,455,100 A | 10/1995 | White | | |
| 5,487,933 A | 1/1996 | White | | |
| 5,552,454 A | 9/1996 | Kretschmann et al. | | |
| 5,571,193 A | 11/1996 | Kampner | | |
| 5,653,765 A * | 8/1997 | McTighe et al. | ............ | 623/22.42 |
| 5,725,592 A * | 3/1998 | White et al. | ................ | 623/23.35 |
| 5,728,510 A | 3/1998 | White | | |
| 5,876,459 A * | 3/1999 | Powell | ......................... | 623/23.15 |

(Continued)

OTHER PUBLICATIONS

"Artificial Bone Grafts:Pro Osteon", http://www.arthroscopy.com/sp12013.htm, Copyright 1999, 4 sheets.

(Continued)

*Primary Examiner* — Alvin J. Stewart
(74) *Attorney, Agent, or Firm* — Harness, Dickey (57) ABSTRACT

A bone augment for repairing a bone defect. The bone augment includes a porous body and a metallic liner. The porous body defines a bore and is configured to be intraoperatively shaped to correspond to the bone defect. The metallic liner is injection molded within the bore such that portions of the liner interlock with pores of the porous body. The metallic liner is operable to mount an implant to the bone augment.

13 Claims, 8 Drawing Sheets

U.S. PATENT DOCUMENTS

| | | | |
|---|---|---|---|
| 5,879,391 A * | 3/1999 | Slamin | 623/20.15 |
| 5,879,394 A * | 3/1999 | Ashby et al. | 623/20.33 |
| 5,902,340 A * | 5/1999 | White et al. | 128/898 |
| 5,906,644 A * | 5/1999 | Powell | 623/20.15 |
| 5,931,871 A * | 8/1999 | Baur et al. | 623/22.4 |
| 5,976,188 A * | 11/1999 | Dextradeur et al. | 623/23.23 |
| 5,977,204 A | 11/1999 | Boyan et al. | |
| 5,986,169 A * | 11/1999 | Gjunter | 424/422 |
| 6,008,430 A | 12/1999 | White | |
| 6,156,070 A * | 12/2000 | Incavo et al. | 623/23.52 |
| 6,224,602 B1 | 5/2001 | Hayes | |
| 6,264,698 B1 * | 7/2001 | Lawes et al. | 623/22.12 |
| 6,264,699 B1 * | 7/2001 | Noiles et al. | 623/23.23 |
| 6,296,667 B1 | 10/2001 | Johnson et al. | |
| 6,302,888 B1 | 10/2001 | Mellinger et al. | |
| 6,319,286 B1 * | 11/2001 | Fernandez et al. | 623/23.18 |
| 6,342,157 B1 | 1/2002 | Hood, III | |
| 6,344,496 B1 | 2/2002 | Niederauer et al. | |
| 6,364,881 B1 | 4/2002 | Apgar et al. | |
| 6,376,573 B1 | 4/2002 | White et al. | |
| 6,464,728 B1 * | 10/2002 | Murray | 623/22.42 |
| 6,518,328 B2 | 2/2003 | Kumar | |
| 6,520,994 B2 * | 2/2003 | Nogarin | 623/19.14 |
| 6,524,342 B1 * | 2/2003 | Muhlhausler et al. | 623/19.14 |
| 6,524,345 B1 | 2/2003 | Valimaa et al. | |
| 6,527,810 B2 * | 3/2003 | Johnson et al. | 623/23.56 |
| 6,565,884 B2 | 5/2003 | Nimni | |
| 6,626,950 B2 | 9/2003 | Brown et al. | |
| 6,632,247 B2 * | 10/2003 | Boyer et al. | 623/23.6 |
| 6,706,072 B2 | 3/2004 | Dwyer et al. | |
| 6,716,250 B2 * | 4/2004 | Ganjianpour | 623/22.42 |
| 6,723,129 B2 * | 4/2004 | Dwyer et al. | 623/22.42 |
| 6,843,805 B2 * | 1/2005 | Webb et al. | 623/17.16 |
| 6,843,808 B2 * | 1/2005 | Grundei | 623/32 |
| 6,869,450 B2 * | 3/2005 | Grundei | 623/32 |
| 6,875,239 B2 * | 4/2005 | Gerbec et al. | 623/23.15 |
| 6,887,276 B2 * | 5/2005 | Gerbec et al. | 623/18.11 |
| 6,981,991 B2 * | 1/2006 | Ferree | 623/23.46 |
| 7,018,420 B2 * | 3/2006 | Grundei | 623/32 |
| 7,097,664 B2 * | 8/2006 | Despres et al. | 623/22.42 |
| 7,105,026 B2 | 9/2006 | Johnson et al. | |
| 7,122,056 B2 * | 10/2006 | Dwyer et al. | 623/22.43 |
| 7,156,880 B2 | 1/2007 | Evans et al. | |
| 7,166,133 B2 * | 1/2007 | Evans et al. | 623/23.51 |
| 7,175,664 B1 * | 2/2007 | Lakin | 623/19.14 |
| 7,189,263 B2 | 3/2007 | Erbe et al. | |
| 7,192,448 B2 * | 3/2007 | Ferree | 623/18.11 |
| 7,431,874 B2 | 10/2008 | Muratoglu et al. | |
| 7,435,263 B2 * | 10/2008 | Barnett et al. | 623/19.12 |
| 7,445,639 B2 * | 11/2008 | Metzger et al. | 623/20.15 |
| 7,470,289 B2 * | 12/2008 | Brehm | 623/20.15 |
| 7,497,874 B1 * | 3/2009 | Metzger et al. | 623/20.15 |
| 7,582,092 B2 * | 9/2009 | Jones et al. | 606/102 |
| 7,691,150 B2 * | 4/2010 | Cronin et al. | 623/20.32 |
| 7,740,662 B2 * | 6/2010 | Barnett et al. | 623/20.33 |
| 7,794,503 B2 * | 9/2010 | Daniels et al. | 623/22.11 |
| 7,854,737 B2 * | 12/2010 | Daniels et al. | 606/102 |
| 7,857,858 B2 * | 12/2010 | Justin et al. | 623/20.34 |
| 7,909,883 B2 * | 3/2011 | Sidebotham | 623/23.55 |
| 7,951,205 B2 * | 5/2011 | McCleary et al. | 623/23.15 |
| 8,100,982 B2 * | 1/2012 | Heck et al. | 623/20.35 |
| 8,163,028 B2 * | 4/2012 | Metzger et al. | 623/20.36 |
| 8,241,367 B2 * | 8/2012 | Justin et al. | 623/20.34 |
| 2002/0004685 A1 * | 1/2002 | White | 623/23.15 |
| 2002/0143403 A1 | 10/2002 | Vaidyanathan et al. | |
| 2003/0065397 A1 * | 4/2003 | Hanssen et al. | 623/20.32 |
| 2003/0109878 A1 * | 6/2003 | Grundei | 606/53 |
| 2003/0139818 A1 * | 7/2003 | Rogers et al. | 623/23.47 |
| 2004/0162619 A1 * | 8/2004 | Blaylock et al. | 623/20.16 |
| 2004/0243248 A1 * | 12/2004 | Despres et al. | 623/22.42 |
| 2004/0254646 A1 * | 12/2004 | Stone et al. | 623/23.15 |
| 2005/0010304 A1 * | 1/2005 | Jamali | 623/23.46 |
| 2005/0075641 A1 | 4/2005 | Singhatat et al. | |
| 2005/0278034 A1 | 12/2005 | Johnson et al. | |
| 2006/0020346 A1 * | 1/2006 | Hunter et al. | 623/23.51 |
| 2006/0173550 A1 * | 8/2006 | Ragbir | 623/22.46 |
| 2007/0021838 A1 | 1/2007 | Dugas et al. | |
| 2007/0088443 A1 * | 4/2007 | Hanssen et al. | 623/23.46 |
| 2007/0135924 A1 * | 6/2007 | Verhoogen | 623/18.11 |
| 2009/0149963 A1 * | 6/2009 | Sekel | 623/20.15 |
| 2009/0306787 A1 * | 12/2009 | Crabtree et al. | 623/20.34 |
| 2010/0114314 A1 * | 5/2010 | Lomicka et al. | 623/16.11 |
| 2010/0145452 A1 * | 6/2010 | Blaylock et al. | 623/16.11 |
| 2010/0241239 A1 * | 9/2010 | Smith | 623/22.42 |
| 2011/0160870 A1 * | 6/2011 | Baumgartner et al. | 623/23.61 |
| 2011/0178604 A1 * | 7/2011 | Porter | 623/19.14 |
| 2011/0196503 A1 * | 8/2011 | Anapliotis et al. | 623/18.11 |
| 2011/0208189 A1 * | 8/2011 | Faccioli et al. | 606/62 |

OTHER PUBLICATIONS

Bio-Medicine; Pro Osteon Bone Graft Substitutes (2pgs).
Pro Osteon® 200R Bone Graft Substitute, Medcompare, Copyright 2003-2009, (2pgs).
Pro Osteon® 500R; Biomet, Copyright 2009 (1 pg).
Pro Osteon® Biomet 200R (1pg).
The Natural Facts About Pro Osteon Implant 500, Interpore International (6pgs).

* cited by examiner

METHOD AND APPARATUS FOR AUGMENTING BONE DEFECTS

FIELD

The present disclosure relates to methods and apparatus for augmenting bone defects.

BACKGROUND

This section provides background information related to the present disclosure and is not necessarily prior art.

Bone damage and/or bone loss can occur, for example, due to disease, trauma, and/or birth defects. Bone implants or augments can be used to repair such damaged bone. Bone augments are often manufactured from metal and have a permanent shape and size, thereby providing only limited restoration of bone stock. A bone augment that can be completely remodeled into bone over time and be modified intraoperatively would be desirable.

SUMMARY

This section provides a general summary of the disclosure, and is not a comprehensive disclosure of its full scope or all of its features.

The present teachings provide for a bone augment for repairing a bone defect. The bone augment includes a porous body and a metallic liner. The porous body defines a bore and is configured to be intraoperatively shaped to correspond to the bone defect. The metallic liner is injection molded within the bore such that portions of the liner interlock with pores of the porous body. The metallic liner is operable to mount an implant to the bone augment.

The present teachings also provide for a bone augment for repairing a bone defect that includes a porous body and a metallic liner. The porous body defines a bore and is configured to be intraoperatively shaped to correspond to the bone defect. The metallic liner is secured within the bore.

The present teachings also provide for a bone augment for repairing a bone defect that includes a bone engaging body and an exterior surface. The bone engaging body defines a plurality of pores. The body is configured to be intraoperatively shaped to correspond to the bone defect. An exterior surface of the bone engaging body includes a polymeric reinforcement member mounted thereto. The reinforcement member is operable to be intraoperatively shaped to correspond to the bone defect.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

A bone augment according to the present teachings is illustrated in FIGS. 1A-3 at reference numeral 10. The augment 10 includes a body 11 having a biocompatible construct that defines a plurality of pores 12, that can include a strengthening component 14. The augment 10 can be intraoperatively shaped as desired to fill a bone defect of most any size or shape, such as a defect in cancellous bone. The augment 10 can include a density similar to that of cancellous bone.

Figure 1A:
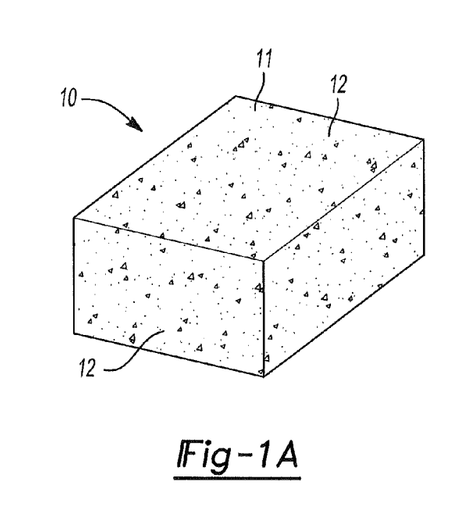
FIG. 1A is a perspective view of a bone augment according to the present teachings prior to being shaped to correspond to a particular bone defect.
Figure 1B:
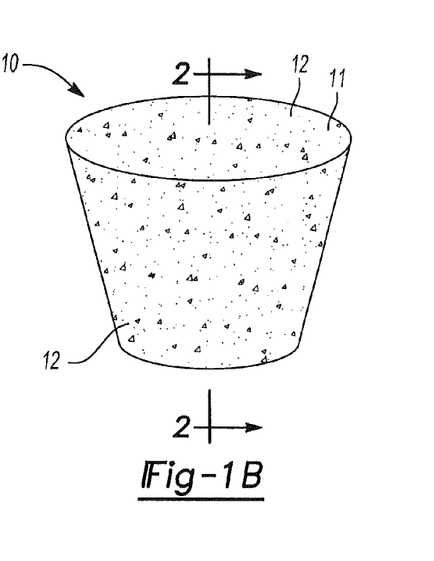
FIG. 1B is a perspective view of the bone augment of FIG. 1A after being shaped to correspond to a particular bone defect.

The augment 10 can be made of any suitable porous material, such as a ceramic or coral, which can be remodeled to bone. Suitable corals include coral hydrothermically converted to hydroxyapatite, such as any of the Pro Osteon® family of bone augments by Biomet of Warsaw, Ind., including Pro Osteon® 200R and 500R for example, which have pore sizes of about 200 and 500 microns respectively. Pro Osteon® is offered in various shapes and sizes, such as a square or rectangular block, as illustrated in FIG. 1A. Using a suitable cutting device, such as a scalpel, saw, or rongeurs, a block of Pro Osteon® can be shaped intraoperatively in any suitable manner, such as to provide a wedge-shaped augment 10 illustrated in FIG. 1B, in order to fill a bone defect of most any shape or size. Pro Osteon is further described in U.S. Pat. No. 3,929,971 (issued Dec. 30, 1975 to Roy) and U.S. Pat. No. 4,976,736 (issued Dec. 11, 1990 to White et al.), which are hereby incorporated by reference. The porous construct of the augment 10 provides a matrix for new bone ingrowth to facilitate healing.

Figure 2:
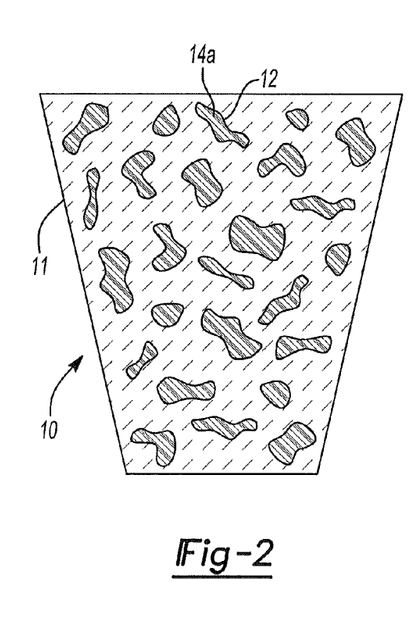
FIG. 2 is a cross-sectional view of the bone augment of FIG. 1B taken along line 2-2 and showing pores of the bone augment filled with a polymeric material.
Figure 3:
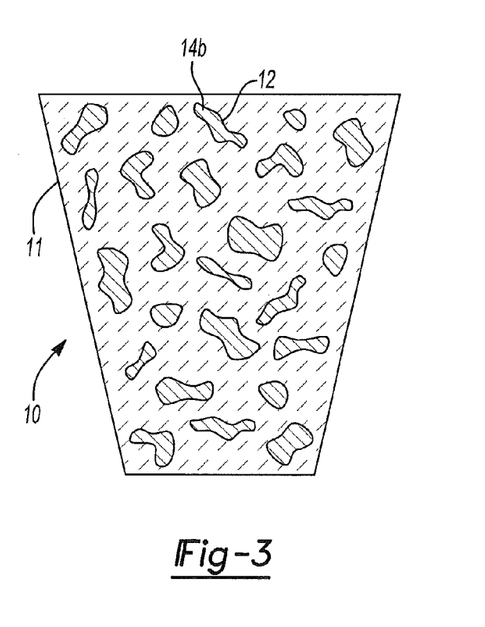
FIG. 3 is a cross-sectional view of the bone augment of FIG. 1B with the pores of the bone augment filled with a metallic material.

As illustrated in FIGS. 2 and 3, the augment 10 can include the strengthening component 14 within the pores 12 to enhance the mechanical strength of the augment 10. The strengthening component 14 can be inserted in the augment 10 in any suitable manner, such as by being injected into the pores 12. The strengthening component 14 can be provided such that it fills all of the pores 12, or only a portion of the pores 12. Upon implantation at a defect site, the body 11 resorbs and bone grows into voids previously occupied by the body 11, as well as into any of the pores 12 left unoccupied by the strengthening component.

The strengthening component 14 can include any suitable biocompatible component, such as a suitable polymer or non-metal 14A (FIG. 2), or a suitable metal 14B (FIG. 3). Suitable polymers and non-metals include one or more of the following: ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as described in U.S. Pat. No. 7,431,874 and all continuation applications and patents related thereto, which are incorporated herein by reference. An exemplary vitamin E stabilized HXLPE that may be used includes E-Poly™ offered by Biomet Orthopedics, Inc. of Warsaw, Ind. Suitable metals include, for example, CoCr, titanium, and combinations thereof. Use of the strengthening component 14 is optional.

Figures 4, 5, 5A, 5B:
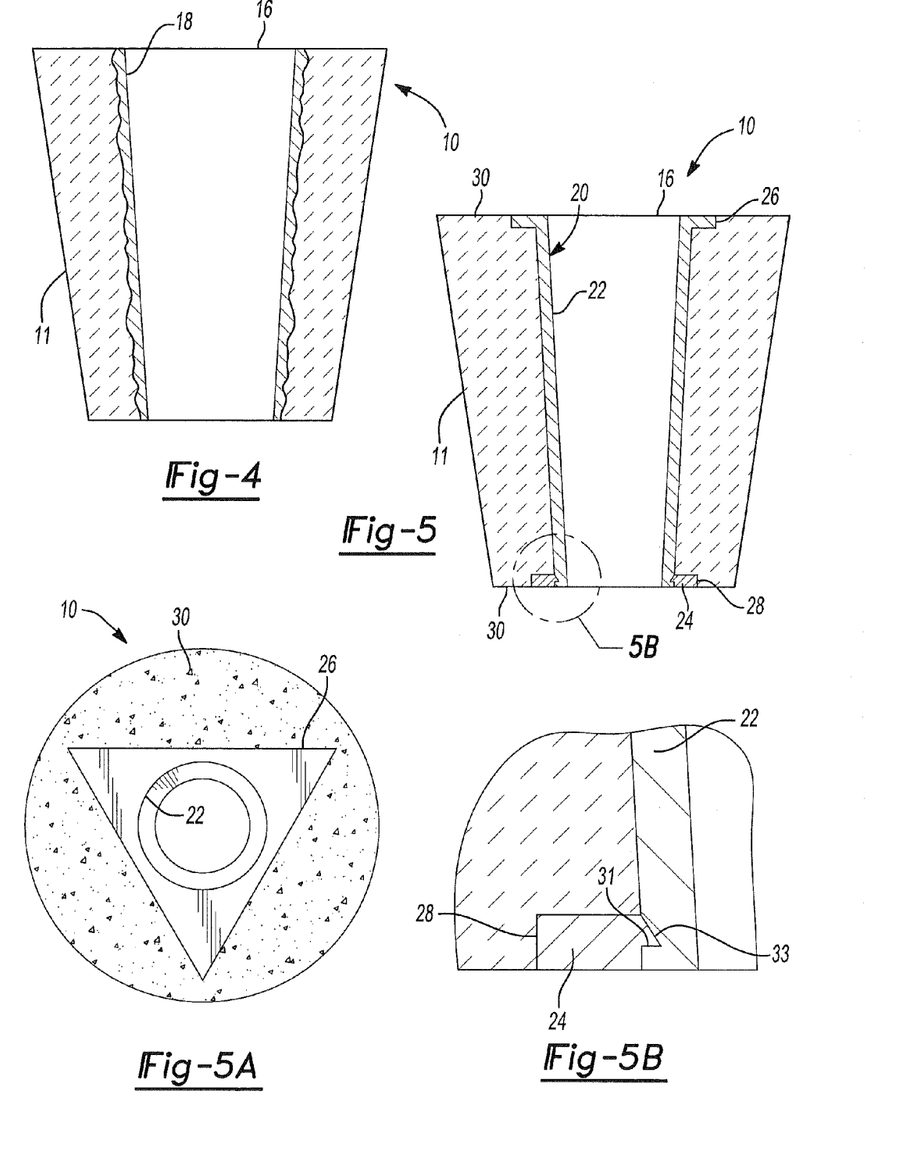
FIG. 4 is a cross-sectional view of the bone augment of FIG. 1B with a metallic sleeve mounted within a bore of the bone augment.
FIG. 5 is a cross-sectional view of the bone augment of FIG. 1B with a metallic insert mounted within the bore of the bone augment.
FIG. 5A is a top view of the bone augment of FIG. 5.
FIG. 5B illustrates the detail at area 5B of FIG. 5.

With additional reference to FIG. 4, the body 11 of the augment 10 can define a bore 16 extending partially or entirely there through. The bore 16 can have any suitable size or shape. For example, the bore 16 can be tapered along its length as illustrated and have a size sufficient to accommodate a stem of a femoral implant therein. The bore 16 can be formed using any suitable cutting device, such as a suitable drill or mill.

The bore 16 can include any suitable liner operable to provide a mechanical connection with an implant, such as a femoral implant stem. The liner increases the strength of the augment 10 to facilitate support of the implant and prevent the augment from possibly fracturing. As illustrated in FIG. 4, the liner can include a tapered metallic sleeve 18 that is metal injection molded into the bore 16 to provide the metallic sleeve 18 with a unitary structure. During the injection molding process, portions of the metallic material enter the pores 12. Upon cooling, the metallic material provides a mechanical interlock with the pores 12 proximate to the bore 16. The tapered sleeve 18 provides a tapered connection with the stem of a femoral implant seated therein, such as a Morse taper lock.

With additional reference to FIGS. 5 and 5A, the liner can include a modular metallic insert 20. The insert 20 includes a main body 22 and a cap 24. The main body 22 includes a first flange 26 and the cap 24 includes a second flange 28. The main body 22 and the cap 24 are positioned in the bore 16 such that the first flange 26 and the second flange 28 are proximate an exterior surface 30 of the augment 10. To accommodate the first flange 26 and the second flange 28, a portion of the exterior surface 30 can be cut out using a suitable cutting device, such as a scalpel, knife, or rongeurs, to permit the first flange 26 and the second flange 28 to be positioned coplanar with the exterior surface 30. In the alternative, the portion of the exterior surface 30 that is cut out can be made in a manufacturing environment, such as with a mill. The first flange 26 and the second flange 28 can also be positioned such that they protrude slightly beyond the exterior surface 30.

The first flange 26 and the second flange 28 can be annular flanges or have any suitable shape to restrict rotation of the insert 20 within the bore 16, such as triangular, square, or hexagonal. The shape of the flanges 26 and 28 can be independent of the shape of the bore 16. For example, FIG. 5A illustrates the first flange 26 having a triangular shape and the main body 22 of the insert 20 having a cylindrical shape. A suitable adhesive can also be provided between the insert 20 and the portion of the body 11 defining the bore 16 to restrict rotation of the insert 20 and retain the insert 20 within the bore 16. Absent the insert 20, friction between the insert 20 and the portion of the body 11 defining the bore 16 can also assist in retaining the insert 20 within the bore 16 and restrict rotation of the insert 20.

As illustrated in FIGS. 5 and 5B, the cap 24 includes a tab 31 that is configured to mate with a recess 33 at an exterior surface of the insert 20 to secure the cap 24 to the main body 22. Thus, after the main body 22 is inserted in the bore 16, the cap 24 is mounted thereto by snapping the tab 31 into the recess 33. The tab 31 and the recess 33 can be annular or there can be multiple tabs 31 and recesses 33 spaced about the cap 24 and main body 22 respectively. Further, the illustrated configuration can be reversed such that the tab 31 can be provided on the main body 22 and the recess 33 is provided in the cap 24.

Figure 5C:
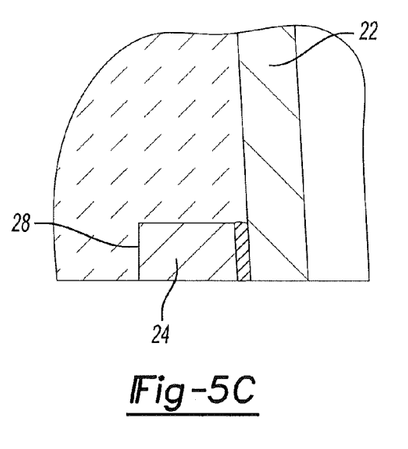
FIG. 5C illustrates an additional arrangement of the detail found at area 5B of FIG. 5.
Figure 5D:
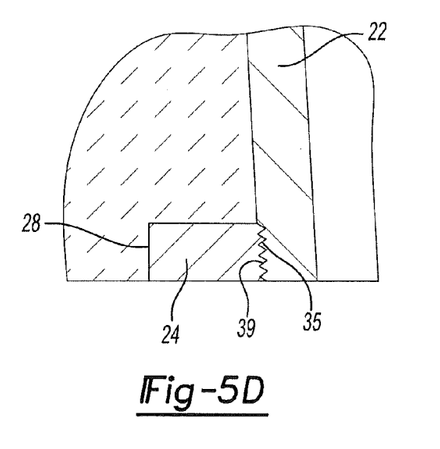
FIG. 5D illustrates another arrangement of the detail found at area 5B of FIG. 5.
Figure 5E:
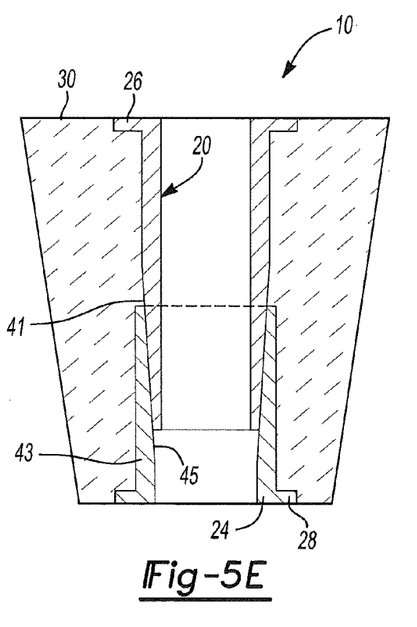
FIG. 5E is a cross-sectional view of the bone augment of FIG. 1B with an additional metallic insert mounted within the bore of the bone augment.

The cap 24 can be mounted to the main body 22 in any suitable manner. For example and with reference to FIG. 5C, the cap 24 can be welded to the main body 22 using a suitable welding device. Further, and with additional reference to FIG. 5D, the main body can include threads 35 that cooperate with threads 39 to allow the cap 24 to be screwed into engagement with the main body 22. Also and with reference to FIG. 5E, the main body 22 can be provided with a first elongated tapered outer surface 41 and the cap 24 can be provided with a stem 43 having a second elongated tapered outer surface 45. The first tapered surface 41 and the second tapered surface 45 are angled such that a Morse taper lock is formed therebetween when the surfaces 41 and 45 are pressed together.

Figure 6:
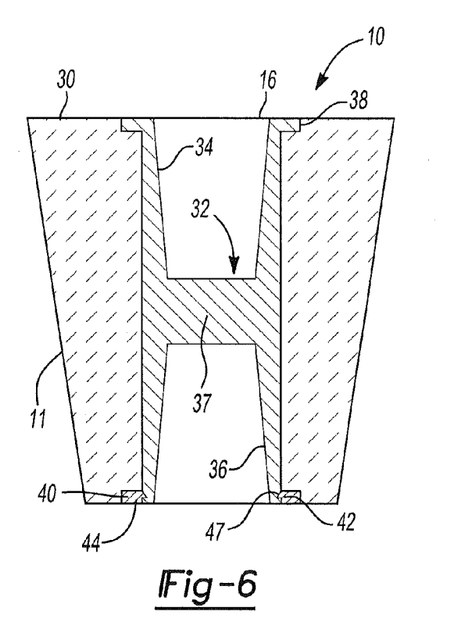
FIG. 6 is a cross-sectional view of the bone augment of FIG. 1B with a taper base mounted within the bore of the bone augment.

With additional reference to FIG. 6, the liner can include a taper base 32 having a first taper 34 and a second taper 36 with a support portion 37 therebetween to provide additional strength and support to the insert 20. The first taper 34 is of any suitable size or shape to provide a Morse taper connection with a suitable implant component, such as a femoral neck for supporting a femoral head. The second taper 36 is of any suitable size or shape to provide a Morse taper connection with another suitable implant component, such as a femoral stem. While the taper base 32 is illustrated as including taper connections 34 and 36, the taper base 32 can include any other suitable attachment feature in place of, or in addition to, the taper connections 34 and 36.

The taper base 32 includes a flange 38 at an end thereof that abuts the exterior surface 30 of the augment 10 when the taper base 32 is seated within the bore 16. A cap 40 interlocks with the taper base 32 in any suitable manner, such as through a snap-fit connection between a tab 42 extending from the cap 40 and a recess 47 in the taper base 32. Further, any of the other connection mechanisms described herein can be used, such as those described in FIGS. 5B-5E.

The cap 40 includes a flange 44 that abuts the exterior surface of the augment 10 to secure the taper base 32 within the bore 16 to restrict axial movement of the taper base 32 within the bore 16. The flanges 38 and 44 are positioned proximate to the exterior surface 30 of the augment 10. To accommodate the flanges 38 and 44, a portion of the exterior surface 30 can be cut out using a suitable cutting device, such as a scalpel, knife, or rongeurs, to permit the flanges 38 and 44 to be positioned coplanar with the exterior surface 30. In the alternative, the portion of the exterior surface 30 that is cut out can be made in a manufacturing environment, such as with a mill. The flanges 38 and 44 can also be positioned such that they protrude slightly beyond the exterior surface 30. The flanges 38 and 44 can be annular flanges or have any suitable shape to restrict rotation of the taper base 32 within the bore 16, such as triangular similar to the shape of the flange 26 of FIG. 5A, square, or hexagonal.

Figure 7:
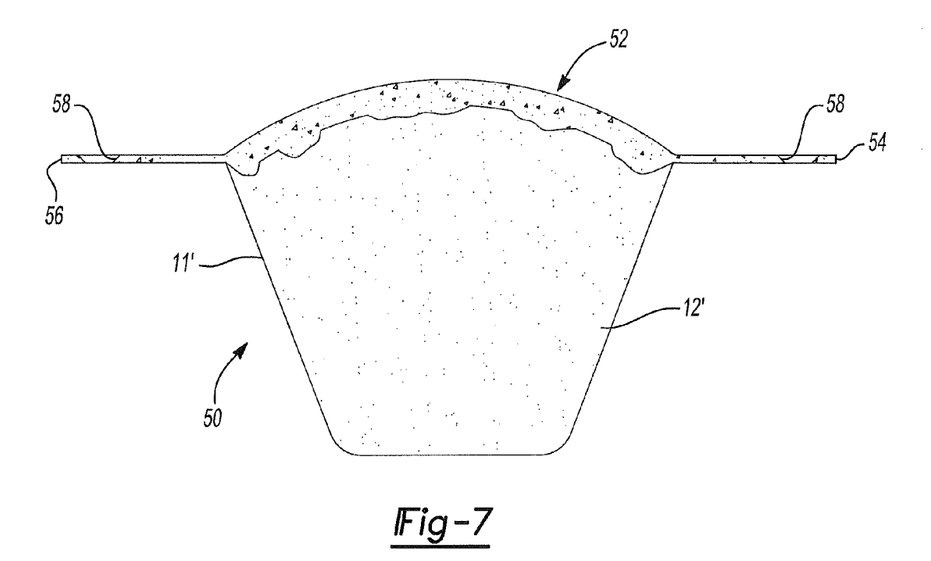
FIG. 7 is a cross-sectional view of a bone augment according to an additional aspect of the present teachings, the bone augment including a reinforcement member mounted thereto.

With additional reference to FIG. 7, another augment according to the present teachings is illustrated at reference numeral 50. The augment 50 can include the same materials and composition as described herein with respect to the augment 10. Thus, the description of the materials and composition of the augment 10 also serves as a description of the augment 50 and need not be repeated. Like the augment 10, the augment 50 includes a body that defines a plurality of pores. The body and pores of the augment 50 are similar to the body 11 pores 12 of the augment 10 and thus are designated with the reference numerals 11' and 12' respectively. The body 11' can replace cancellous bone, as described below.

The augment 50 also includes a reinforcement member 52. The reinforcement member 52 includes a first projection 54 and a second projection 56, each projection 54 and 56 includes an aperture 58 capable of receiving a suitable fastening device, such as a screw 60. The reinforcement member 52 can replace cortical bone, as described further below, and includes a density similar to cortical bone. The reinforcement member 52 can include any suitable biocompatible material, such as one or more metallic or polymeric materials.

Suitable polymers or non-metals include one or more of the following: ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as described in U.S. Pat. No. 7,431,874 and all continuation applications and patents related thereto, which are incorporated herein by reference. An exemplary vitamin E stabilized HXLPE that may be used includes E-Poly or E1™ offered by Biomet of Warsaw, Ind. Suitable metals include, for example, CoCr, titanium, and combinations thereof.

The projections 54 and 56 can be deformed in any suitable manner to match the morphology of a repair site. For example, the projections 54 and 56 can be bent with a suitable instrument (such as pliers or a roll bender, for example), can be pressed into a mold of the implant site, and can be machined during manufacturing to correspond a specific patient's morphology.

The reinforcement member 52 can be mounted to the augment 50 in any suitable matter, such as with injection molding or compression molding. With both injection molding and compression molding, portions of the reinforcement member 52 enter a portion of the pores 12' to provide a mechanical interlock with the pores 12'. As with the augment 50, the reinforcement member 52 can be machined in order to fit a particular defect site. As further discussed herein, the augment with the reinforcement member 52 mounted thereto can be used to fill an uncontained defect, such as at a peripheral portion of a tibia upper extremity, because the reinforcement member 52 can retain the augment 50 in an uncontained defect through cooperation between the screws 60 and surrounding bone.

Figure 8:
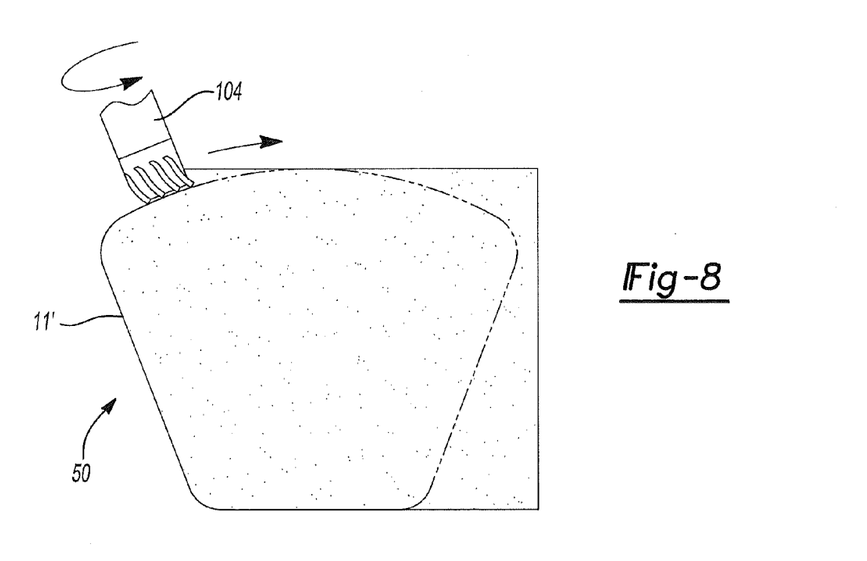
FIG. 8 is a side view of the bone augment of FIG. 1 being intraoperatively shaped to fit a bone defect.

As illustrated in FIG. 8, the augment 50 can be intraoperatively shaped to accommodate a defect. Both the body 11' and the reinforcement member 52 can be shaped. To shape the body 11', a cutting device 104, such as a scalpel, saw, or rongeurs, for example, can be used. To shape the reinforcement member 52, a bur, saw, or rongeurs, for example, can be used.

Figure 9:
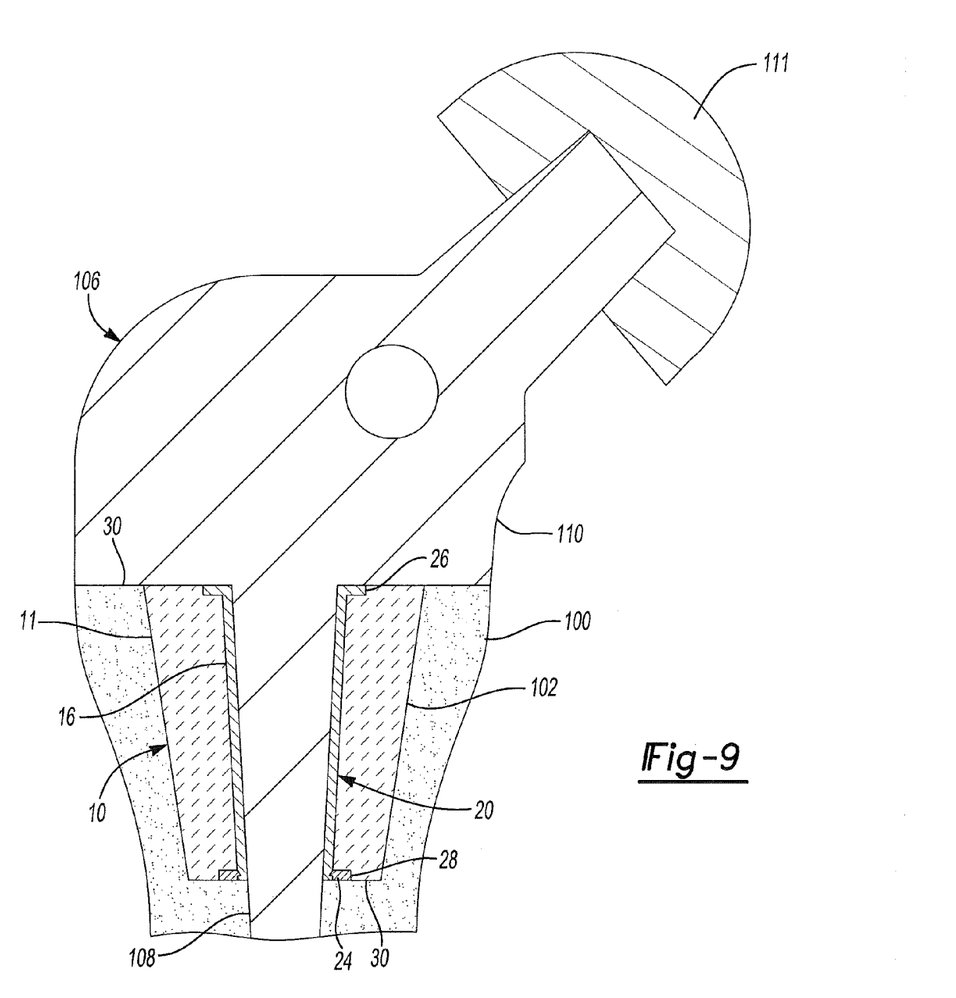
FIG. 9 is a cross-sectional view of the bone augment of FIG. 5 seated within a defect site of a femur to support a femoral implant.

With additional reference to FIG. 9, use of the porous augment 10 in a proximal portion of a femur 100 to fill a defect 102 during a femoral joint replacement is illustrated. The augment 10 includes the bore 16 and the insert 20 mounted therein. The bore 16 is formed therein with a suitable cutting device, such as a suitable drill or mill.

To shape the body 11, a suitable cutting device, such as a scalpel, saw, or rongeurs, for example, can be used. The shaped augment 10 is secured at the defect site 102 in any suitable manner, such as with a press-fit or suitable fastener, to fill damaged cancellous bone. The composition of the augment 10, particularly Pro Osteon®, permits insertion of a fastener into the augment 10 without pre-drilling. Any suitable implant, such as a femoral implant 106 having a stem 108 and a neck 110 supporting a head 111, can be attached to the augment 10 for support. As illustrated, the stem 108 is inserted into the bore 16 to mate with the metallic insert 20, which secures the stem 108 with a press-fit and/or a Morse taper. During the healing process bone grows into the pores 12 of the augment 10 and the augment 10 is remodeled into the femur 100, except for the metallic insert 20.

The insert 20 is optional. When the insert 20 is not used, the stem 108, or any suitable implant, can be secured within the bore 16 with a suitable fastening device or material, such as poly methyl methacrylate ("PMMA") bone cement.

Figure 10:
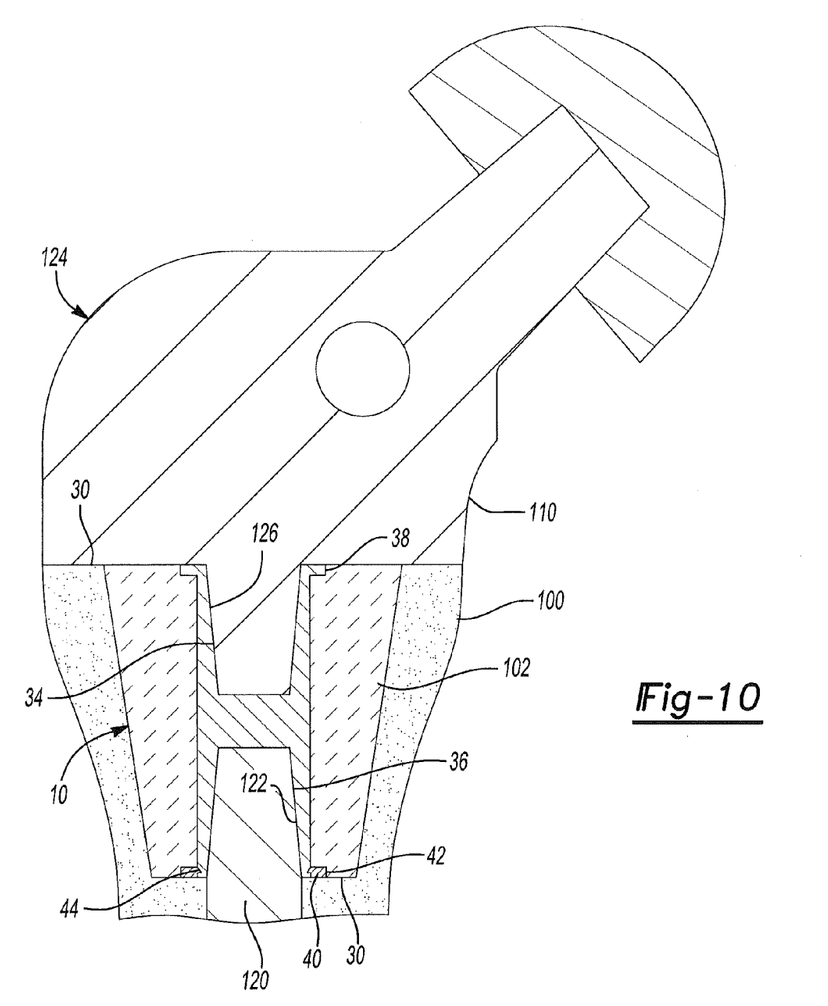
FIG. 10 is a cross-sectional view of the bone augment of FIG. 6 mounted within a defect site of a femur to support a femoral stem implant and a femoral head implant.

With additional reference to FIG. 10, implantation of the augment 10 including the taper base 32 is illustrated. As described previously, the augment 10 is intraoperatively shaped to fill the defect 102 and then secured in the defect 102 in any suitable manner, such as with a press-fit or suitable fastener, to fill damaged cancellous bone. The second taper 36 of the taper base 32 is mounted to a suitable implant, such as a femoral stem implant 120. A taper connection surface 122 of the stem implant 120 is mated with the second taper 36 of the taper base 32 to secure the femoral stem implant 120 to the taper base 32 with a Morse taper. A femoral neck implant 124 having a taper connection 126 is mounted to the taper base 32 through cooperation between the taper connection 126 and the first taper 34 of the taper base 32. During healing the augment 10 is remodeled into the femur 100, except for the taper base 32. As illustrated, the taper connection surface 122 provides the male end of the Morse taper and the second taper 36 provides the female end, but this configuration can be reversed.

Figure 11A:
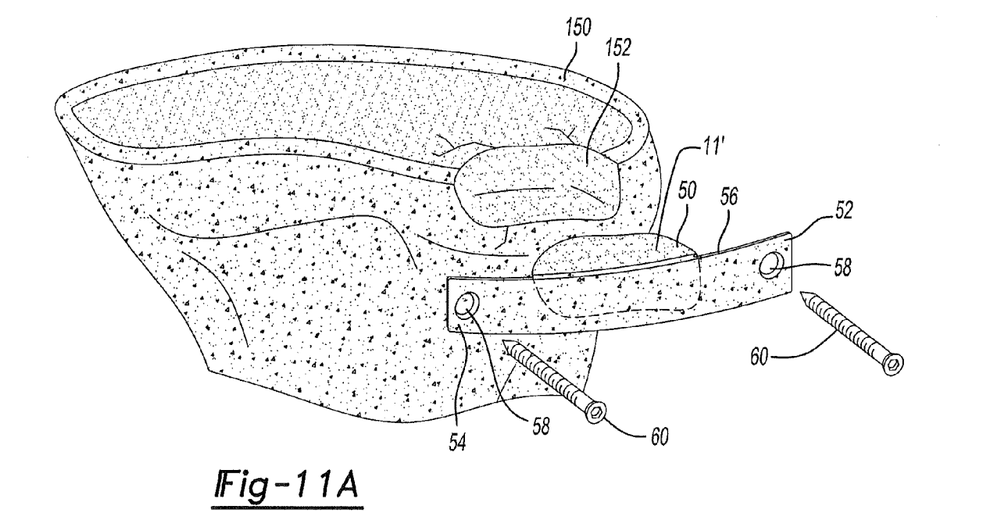
FIG. 11A is a perspective view of the bone augment of FIG. 7 being implanted in a defect site of a tibia bone.
Figure 11B:
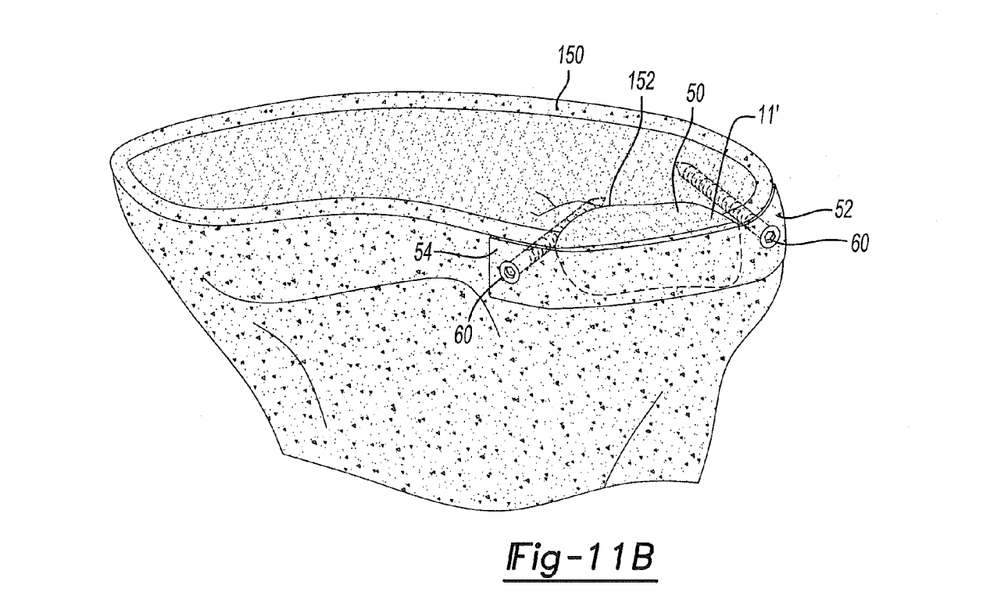
FIG. 11B is a perspective view of the bone augment of FIG. 7 implanted within the defect site of the tibia bone.
Figure 12:
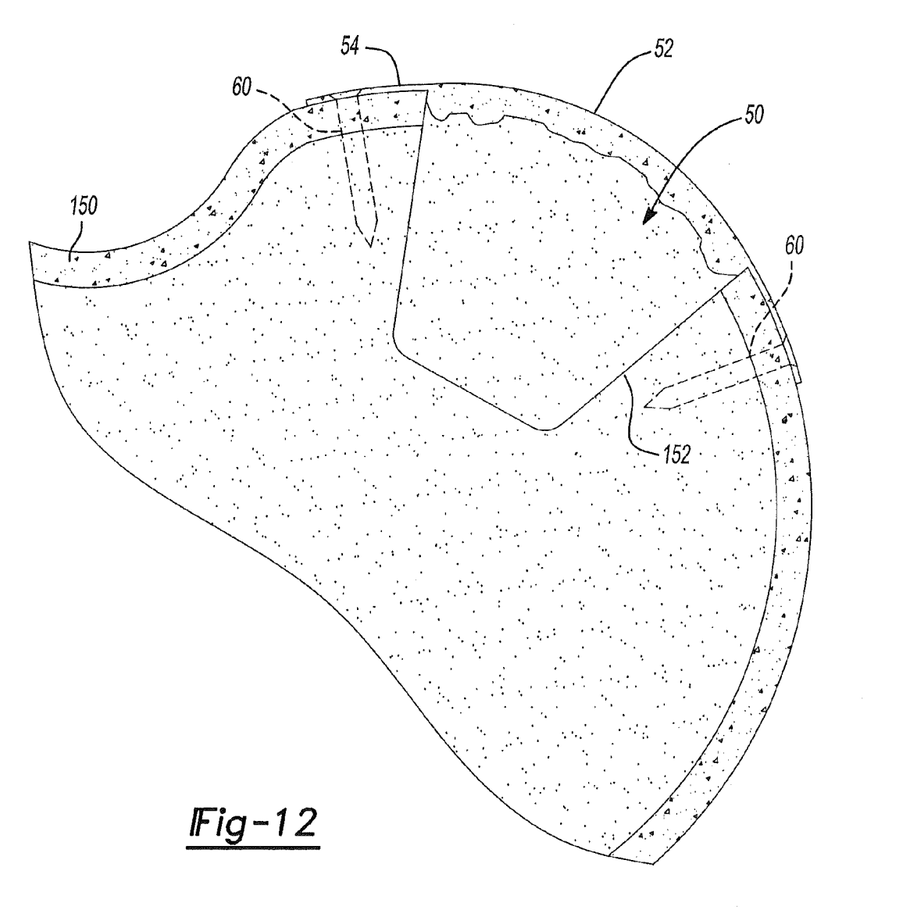
FIG. 12 is a top view of the bone augment of FIG. 7 implanted within the defect site of the tibia bone.

With reference to FIGS. 11A, 11B, and 12, use of the porous augment 50 at an upper extremity of a tibia 150 to fill a defect 152 is illustrated. The augment 50 includes the reinforcement member 52 mounted thereto.

The augment 50 and reinforcement member 52 can each be intraoperatively shaped to accommodate the uncontained defect 152 using a suitable cutting device. To shape the body 11' the cutting device 104, such as a scalpel, saw, or rongeurs, for example, can be used. To shape the reinforcement member 52, a bur, saw, or rongeurs, for example, can be used. The shaped augment 50 is secured at the defect site 152 with the screws 60, which extend through the projections 54 and 56 and into an area of the tibia 150 proximate to the defect 152 having bone of sufficient rigidity to retain the screws 60, such as cortical bone. During the healing process, cancellous bone is permitted to grow into the pores 12' of the augment 50 and the augment 50 is remodeled into the tibia 150, except for the polymeric reinforcement member 52, the rigidity of which serves to replace the missing cortical bone. Thus, the augment 50 is positioned such that the body 11' provides a bone engaging surface and the reinforcement 52 provides a exterior surface.

Use of the augments 10 and 50 in the femur 100 and the tibia 150 is for exemplary purposes only. The bone augments 10 and 50 can be used to repair any suitable defect in suitable bone. To accommodate use of the augments 10 and 50 in bones of various different sizes, various sized augments 10 and 50 can be provided.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A bone augment for repairing a bone defect comprising:
   a porous body that defines a bore, the porous body is configured to be intraoperatively shaped to correspond to the bone defect; and
   a metallic liner secured within the bore, the metallic liner including a first coupling surface within the bore and a second coupling surface within the bore;
   wherein the metallic liner includes a main body having a first locking surface and a cap having a second locking surface that is operable to engage with the first locking surface to secure the cap to the main body.

2. The bone augment of claim 1, wherein the first locking surface includes one of a locking tab and a locking recess, and the second locking surface includes another of the locking tab and the locking recess.

3. The bone augment of claim 1, wherein the main body is secured to the cap by a weld between the first locking surface and the second locking surface.

4. The bone augment of claim 1, wherein the first locking surface includes first threads and the second locking surface includes second threads; and
   wherein the main body is secured to the cap through engagement between the first threads and the second threads.

5. The bone augment of claim 1, wherein the main body includes a first flange and the cap includes a second flange.

6. The bone augment of claim 5, wherein at least one of the first flange and the second flange is annular.

7. The bone augment of claim 1, wherein the first coupling surface includes a first taper lock surface and the second coupling surface includes a second taper lock surface, a support portion is between the first taper lock surface and the second taper lock surface;
   wherein the first taper lock surface is operable to mount a femoral neck implant thereto and the second taper lock surface is operable to mount a femoral stem implant thereto.

8. The bone augment of claim 1, wherein the first coupling surface is aligned with the second coupling surface along a longitudinal axis of the metallic liner.

9. A bone augment for repairing a bone defect comprising:
   a porous body that defines a bore, the porous body is configured to be intraoperatively shaped to correspond to the bone defect; and
   a liner within the bore including a first coupling surface configured to connect a femoral neck implant to the bone augment, and a second coupling surface configured to connect a femoral stem implant to the bone augment, the first coupling surface is a first taper lock surface and the second coupling surface is a second taper lock surface, a support portion of the liner is between the first and the second coupling surfaces;
   wherein the first coupling surface is opposite to, and aligned with, the second coupling surface along a longitudinal axis of the liner.

10. The bone augment of claim 9, wherein the liner is metallic.

11. The bone augment of claim 9, wherein the liner includes a main body having a first locking surface and a cap having a second locking surface that is operable to engage with the first locking surface to secure the cap to the main body.

12. The bone augment of claim 9, wherein the bore extends through the porous body and is tapered from a first end to a second end.

13. The bone augment of claim 9, wherein the first coupling surface and the second coupling surface are both within the bore.

* * * * *